United States Patent [19]
Teleki

[11] Patent Number: 4,764,946
[45] Date of Patent: Aug. 16, 1988

[54] METHOD AND MODIFYING BODY FOR INFLUENCING THE EFFECT OF X-RAY OR GAMMA RADIATION ON A TARGET SENSITIVE TO THE RADIATION

[75] Inventor: Peter Teleki, Bocskai, Hungary

[73] Assignee: Innofinance Altalanos Innovacios Penzwtezet, Budapest, Hungary

[21] Appl. No.: 890,021

[22] PCT Filed: Nov. 5, 1985

[86] PCT No.: PCT/HU85/00061
§ 371 Date: Jul. 7, 1986
§ 102(e) Date: Jul. 7, 1986

[87] PCT Pub. No.: WO86/03032
PCT Pub. Date: May 22, 1986

[30] Foreign Application Priority Data
Nov. 5, 1984 [HU] Hungary .................. 4087/84

[51] Int. Cl.⁴ .......................... G01N 23/04
[52] U.S. Cl. .................. 378/62; 378/156; 378/185; 378/145; 250/482.1; 250/483.1
[58] Field of Search ......... 378/7, 62, 156-159, 378/185-186; 250/482.1, 483.1

[56] References Cited

U.S. PATENT DOCUMENTS

| | | | |
|---|---|---|---|
| 2,541,599 | 2/1951 | Morrison | 378/185 |
| 2,928,946 | 3/1960 | Allisy | 378/157 |
| 3,860,817 | 1/1975 | Carmean | 378/156 |
| 3,872,309 | 3/1975 | DeBelde et al. | 250/483.1 |
| 3,924,127 | 12/1975 | Cheret et al. | 250/483.1 |
| 4,064,440 | 12/1977 | Roder | 378/57 |
| 4,300,046 | 11/1981 | Wahg | 378/62 |
| 4,467,026 | 8/1984 | Ogawa | 378/34 |

FOREIGN PATENT DOCUMENTS

| | | | |
|---|---|---|---|
| 0099285 | 1/1984 | European Pat. Off. | 250/483.1 |
| 0615902 | 1/1949 | United Kingdom | 378/186 |
| 961868 | 6/1964 | United Kingdom | |
| 1272404 | 4/1972 | United Kingdom | |
| 0585470 | 12/1977 | U.S.S.R. | 378/185 |

OTHER PUBLICATIONS

"Definition and Measurement of Means of Filtered X-Radiation", by Grudskii et al., Pribory i Tekhnika Eksperimenta#4, 7-8, 1974.

"Balanced Filters for Silver $K_\alpha$ X-Rays", by Berman et al, Review of Sci. Instruments, vol. 41, No. 6, Jun. 1970.

Radiation Defectoscopy, 2nd Edition, Roumyantsev, S.V., pp. 158-159 and 195-200, Moscow, Russia, 1974 (English Translation Attached).

*Primary Examiner*—Craig E. Church
*Assistant Examiner*—John C. Freeman
*Attorney, Agent, or Firm*—Sughrue, Mion, Zinn, Macpeak and Seas

[57] ABSTRACT

Method and modifying body for influencing the effect of X-ray or gamma radiation on a target (7) sensitive to radiation, in particular for selective modification of a radiograph of an object (10). According to the invention a modifying body comprising at least two layer groups (31, ... 3n) is arranged in front of the target, wherein each layer group (e.g., 32) emits a secondary radiation under the influence of the X-ray or gamma radiation or the secondary radiation of the previous layer group (e.g., 31), respectively, the energy of which is lying above the absorption energy level defined by the electron shell K of an element being present in the following layer group (e.g., 33) or in the target arranged behind the last layer group (3n), respectively.

27 Claims, 1 Drawing Sheet

METHOD AND MODIFYING BODY FOR INFLUENCING THE EFFECT OF X-RAY OR GAMMA RADIATION ON A TARGET SENSITIVE TO THE RADIATION

TECHNICAL FIELD

The invention relates to a method for influencing the effect of X-ray or gamma radiation on a target sensitive to the radiation, preferably for selective modification of an image of an object formed on a target by X-ray or gamma radiation, as well as to a modifying body for implementing the method according to the invention.

BACKGROUND ART

For producing radiographs, amplifying foils are known which convert the incident X-ray radiation into a radiation falling in the range of visible light. In general, these amplifying foils used to be arranged before and behind the film to be shot. In this case blackening of the film is primarily caused by the radiation falling into the visible range. Application of amplifying foils enables reduction of exposure time, however, it is accompanied by a loss in the sharpness of the image.

From the PCT Application PCT/HU83/00062 published under the number WO 84/02399 a method for producing radiographs is known, in which a modifying body of laminar structure is placed between the object to be examined and the film. The modifying body consists of thin Pb layers arranged on one another, which are applied onto a carrier sheet. If in the object examined material thickness corresponding to different ray paths is changing, e.g. the object is a pipe, the modifying body automatically acts as a compensator. In such a manner, on the image thus obtained far more details of the object can be seen and evaluated, however, the exposure times have to be increased.

In radiologic practice materials of the films used for preparing radiographs respond only to an X-ray or gamma radiation, the energy of which surpasses a given limit of energy level. In general, sensitivity is the highest immediately above said energy level, thereafter with increasing energy it drops considerably. Just in order to eliminate this dependency on energy, sensitivity of usual films used to be modified by means of filters so as to achieve nearly equal sensitivity in a broader range of energy. This, however, involves a poor sensitivity of the film in the whole energy range, requiring an increased radiation intensity or a longer exposure time in preparing radiographs.

DISCLOSURE OF INVENTION

The aim of the invention is to develop a method and means, by the aid of which an image formed by X-ray or gamma radiation can be advantageously influenced so that quality of the image could be improved without prolonging the exposure time, and if possible, even with a shorter exposure period.

Accordingly, the invention relates to a method for influencing the effect of X-ray or gamma radiation on a target sensitive to the radiation, preferably for selective modification of an image of an object formed on a target by X-ray or gamma radiation, in the course of which a modifying body having laminar structure is arranged in front of the target in the path of the radiation beam. The improvement according to the invention is that in front of the target at least two layer groups are disposed, each of said layer groups comprises a plurality of superimposed layers emitting a secondary radiation under the influence of the primary radiation or the secondary radiation of the previous layer group, respectively, the energy of which is lying above the absorption energy level defined by the electron shell K of an element being present in the following layer group or in the target arranged behind the last layer group, respectively.

By proper selection of the material of said layer groups it can be achieved that at least a part of the primary X-ray or gamma radiation is converted gradually within the layer groups into a radiation with an energy range in which the sensitivity of the target is maximal. By the better utilization of the target a reduction of exposure time becomes possible. The target can be a film being sensitive to X-ray or gamma radiation or a screen or any image-sensing means, e.g. a NaI or CsI crystal detector doped by Tl.

It has also been recognized that it can be advantageous, if a layer group is disposed in front of the target, with which the energy of the secondary radiation emitted by said layer group is lying between the absorption energy level and the emission energy level defined by the electron shell K of an element being present in the following layer group or in the target. By means of this secondary radiation the following layer group or the target can be pre-excited, accordingly, it will be more sensitive to the radiation with an energy lying above the absorption energy level.

In accordance with the invention, material and location of the layer groups are to be selected expediently so that when progressing in a direction toward the target, the successive layer groups should contain elements with ever decreasing atomic numbers.

Sharpness of the radiograph thus obtained can be increased if at the layer groups an electric field with a direction corresponding or opposite to the radiation beam is generated, e.g. so that a proper voltage is applied onto the insulated Al layers formed on the two extreme boundary surfaces of the layer groups lying above one another. In such a manner electrons generated by the X-ray or gamma radiation can be well controlled.

For absorbing scattered radiation arriving from the object to be examined and from the environment it is expedient to dispose Pb layers between the object tested and the first layer group facing the object. In order to absorb re-scattered radiation it can be advantageous to dispose Pb layers lying on one another behind the target.

The invention also relates to a modifying body for influencing the effect of X-ray or gamma radiation on a target sensitive to such radiations, said modifying body comprises a plurality of superimposed layers. The modifying body according to the invention comprises at least two superimposed layer groups, each layer group comprising a plurality of superimposed layers containing an element which emits a secondary radiation under the influence of the X-ray or gamma radiation or the secondary radiation of the previous layer group, respectively, the energy of which is lying above the absorption energy level defined by the electron shell K of an element being present in the following layer group or in the target, respectively.

It is considered as advantageous for the sake of the aforementioned pre-excitation that the modifying body comprises a layer group which contains an element emitting a secondary radiation, the energy of which is lying between the absorption energy level and the emission energy level defined by the electron shell K of an element being present in the following layer group or in the target, respectively.

Advantageously, layer thickness in the modifying body according to the invention is less than 100 μm, expediently less than 30 μm. Most advantageously the thickness lies in the range between 0.1 and 10 μm, in this case namely the radiation is compelled to travel through a plurality of boundary surfaces, which involves an increased probability of interactions and thus the increase of absorption of the primary radiation.

In case the Compton-effect dominates in the modifying body, it can be advantageous to use one or more layers or coatings consisting of graphite or carbon or a carbon compound in the modifying body.

It can be expedient, if the surfaces of the layers of the modifying body are provided with substantially monoatomic coatings which reduce the escape energy of electrons, consisting of alkali metal or alkali-earth metal or the oxides thereof or any other compound thereof. A positive ion reduces the potential barrier of the constituent element of the layer, representing the pre-requisite for the tunnel effect. Evaporation of the coating is not to be feared, accordingly, $Li_2O$ ... $Cs_2O$ compounds, as well as oxides of alkali-earth metals are well suitable for this purpose. One has to reckon also with a secondary electron emission, for which purpose the coatings are well-suited, too. Due to the secondary electron emission, smoothness of surfaces is imperative, otherwise the electrons are easily trapped on the porous surface.

In respect to the arrangement of the modifying body in an electric field it is advantageous, if there is at least one layer made of a conductive material—preferably of Al—being insulated from the other layers and provided with an electric contact and a terminal connected thereto.

The modifying body according to the invention can be prepared so that all layers of a layer group are applied onto a carrier sheet being substantially transparent for X-ray or gamma radiation, and between the layers separating layers are inserted. According to another embodiment all the layers of all layer groups are applied to one single carrier sheet one after the other. The carrier sheet can be made of paper or plastic or aluminium foil. It is considered as very advantageous, if all the layers as well as the separating layers inserted inbetween—e.g. made of $Al_2O$—are applied onto a single carrier sheet by vacuum deposition. In the same manner, most easily, eventual coatings on the layers can be applied also by evaporation.

If an AgBr film is used as a target, from the point of view of sensitivity, expediently a modifying body is to be selected, with which the energy of the secondary radiation emitted by the element of the last layer group surpasses by 100% at most, preferably by a maximum of 50%, the absorption energy level of the element of the target.

BRIEF DESCRIPTION OF THE DRAWING

The invention will be described in detail by means of preferred embodiments serving as examples, with the aid of the drawing enclosed, wherein.

MODES FOR CARRYING OUT THE INVENTION

Figure 1:
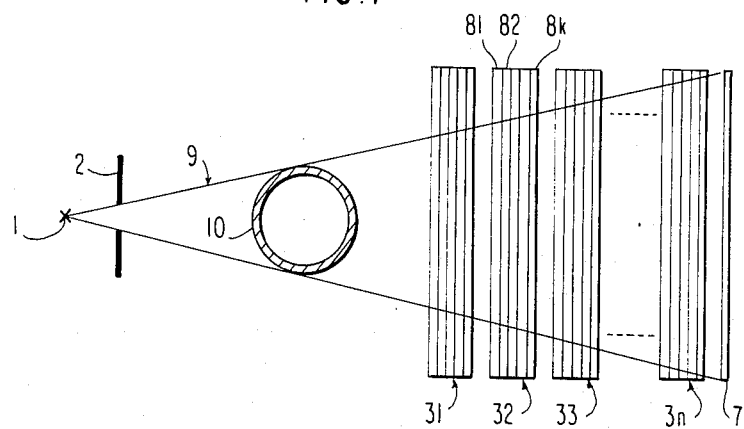
FIG. 1 is a schematical view of the modifying body according to the invention and the application thereof according to the invention.
Figure 2:
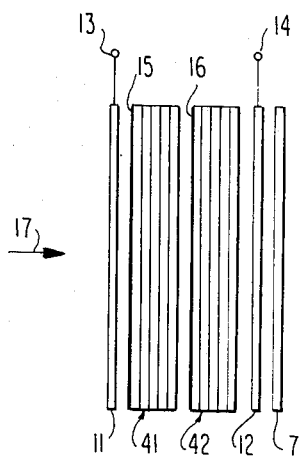
FIGS. 2 to 3 are schematical views of embodiments of the modifying body according to the invention being suitable for an X-ray film target.
Figure 3:
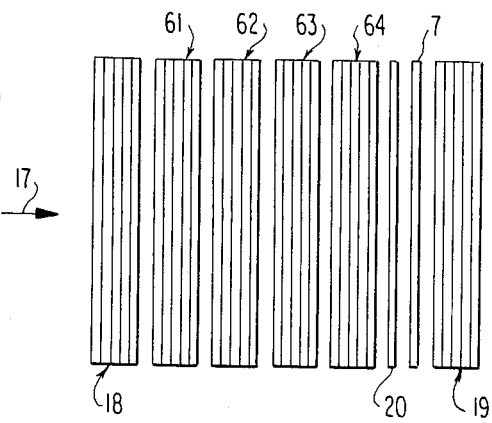

In FIG. 1 a radiation beam 9 emitted onto an object 10 to be examined by a radiation source 1, which can be a usual industrial X-ray apparatus, is confined by an aperture 2. Due to the radiation beam 9 travelling through the object 10 radiograph of the object 10 appears on the target 7, e.g. on an X-ray film. The modifying body according to the invention is arranged between the object 10 and the target 7, in front of the target 7. The modifying body consists of n layer groups 31, 32, 33, . . . 3n which are superposed on one another and are lying approximately perpendicularly to the radiation beam 9. Every layer group is composed of a plurality of layers superposed on each other, so e.g. the layer group 32 contains k layers 81, 82, . . . 8k. Adjacent layers e.g. 81 and 82 are separated by a thin separating layer (not shown). For the sake of visibility in FIG. 1 layers and layer groups are not illustrated according to the actual scale, and similarly, FIGS. 2 and 3 are not accurately scaled, either.

If the target 7 is an AgBr X-ray film being sensitive to X-ray radiation, materials of the layer groups 31, 32, 33, . . . 3n are selected so that the energy of the X-ray beam entering into the first layer group 31 will be transposed gradually by the layer groups into the range of maximum sensitivity of the X-ray film forming the target 7. Hereinafter, before symbols of the elements the atomic number Z will always be indicated. The energy level of absorption defined by the electron shell K of an element, representing the limit value of excitation of said element, expressed in unit keV, will be indicated with K. The most probable energy levels of emission corresponding to the transition between the electron shells K and L of the excited element, expressed also in unit keV, are marked with $\alpha 1$ and $\alpha 2$. For the aforementioned gradual energy transposition the constituent elements of the layer groups 31, . . . 3n for the AgBr X-ray film can be selected according to the following columns:

| 44Ru | 60Nd |
|---|---|
| K = 22.12 | K = 43.57 |
| α1 = 19.28 | α1 = 37.36 |
| α2 = 19.15 | α2 = 36.84 |
| ↓ | ↓ |
| 41Nb | 55Cs |
| K = 18.99 | K = 35.98 |
| α1 = 16.61 | α1 = 30.97 |
| α2 = 16.52 | α2 = 30.62 |
| ↓ | ↓ |
| 38Sr | 51Sb |
| K = 16.11 | K = 30.49 |
| α1 = 14.16 | α1 = 26.36 |
| α2 = 14.10 | α2 = 26.11 |
| ↓ | ↓ |
| 35Br | 47Ag |
| K = 13.47 | K = 25.51 |
| α1 = 11.92 | α1 = 22.16 |
| α2 = 11.88 | α2 = 21.99 |

As it becomes obvious from the columns, the elements are to be selected so that the energy of the exciting radiation falling onto the element should surpass the energy level K of absorption, at the same time the emission energy levels α1 and α2 of the characteristic radiation emitted by the excited element should be higher than the absorption energy level K of the following element. The series of excitation of 35Br prior to 44Ru can be as follows: 74W—68Er—62Sm—57La—52-Te—48Cd. The series of excitation of 47Ag prior to 60Nd can be as follows: 78Pt—71Lu—65Tb. In respect to the practice here the series can be closed.

Limit energy level of sensitivity of AgBr X-ray film is defined by the absorption energy level K of 47Ag. However, we found that it is advantageous if energy of radiation falling onto the X-ray film is fitted also to 35Br, e.g. in accordance with the previously described 35Br series, as in such a manner efficiency of blackening of the X-ray film can be increased.

FIG. 2 illustrates a modifying body with such a layer arrangement wherein in the path of the radiation beam arriving in the direction as indicated by arrow 17 a layer group 41 containing layers with 51Sb material is arranged first, followed by a layer group 42 containing layers with 38Sr material. Emission energy levels $\alpha 1$ and $\alpha 2$ of characteristic radiation emitted by 51Sb are on the one hand fitted to the absorption energy level K of the component 47Ag of the AgBr X-ray film i.e. to the target 7, and on the other hand higher than the absorption energy level of 38Sr. As a consequence, the latter will be excited. Energy levels $\alpha 1$ and $\alpha 2$ of characteristic radiation emitted by 38Sr are matched to the absorption energy level K of 35Br. Accordingly, the layer group 42 containing layers with 38Sr material allows to pass a part of the incident radiation to the target 7, while the other part is absorbed and emits instead a radiation with an energy matched to 35Br.

In addition, the modifying body according to FIG. 2 is provided with two graphite coatings 15 and 16, which are—with the embodiment described here—applied onto the first layers of the layer groups 41 and 42. Graphite coatings 15 and 16 contain 6C with a low absorption energy level K, behaving as an electron donor. Layers of the layer groups 41 and 42 can be additionally provided with a mono-atomic coating (not shown) reducing the escape energy of electrons. Layer groups 41 and 42 are surrounded by layers 11 and 12 of Al-material, serving as plates for generating an electric field, and they are connected with terminals 13 and 14 via contacts not illustrated here. By insertion of an insulating layer, the layers 11 and 12 can be applied onto the layer groups 41 and 42 by evaporation.

In the modifying body according to the invention, from the series of elements having been described in connection with FIG. 1, one or more members may be left out. In the course of transposition of energy level larger steps are also permitted.

In FIG. 3 a modifying body for an AgBr X-ray film target 7 can be seen, in which in the path of the radiation beam coming in the direction as indicated by the arrow 17 layer groups 61, 62, 63 and 64 are arranged one after the other. Layers of the layer group 61 contain 51Sb or its compound, layers of the layer group 62 contain 50Sn or its compound, layers of the layer group 63 contain 38Sr or its compound and layers of the layer group 64 contain 37Rb or its compound. In this embodiment elements 51Sb and 38Sr play the same role as in the embodiment according to FIG. 2, that means that 51Sb is matched to the component 47Ag of the X-ray film and 38Sr to the component 35Br.

The role of the elements 50Sn and 37Rb is in producing a radiation for the component 47Ag and 35Br, respectively, the energy level of which is lower than the corresponding absorption energy level K, however it is advantageously higher than the corresponding $\oplus 1$ energy level. In such a manner atoms 47Ag and 35Br are pre-excited in order to obtain a better efficiency with respect to the absorption of the radiation emitted by 51Sb and 38Sr, respectively. So e.g.

| 50Sn | → | 47Ag |
|---|---|---|
| K = 29.20 | | K = 25.51 |
| $\alpha 1$ = 25.27 | | $\alpha 1$ = 22.16 |
| $\alpha 2$ = 25.04 | | $\alpha 2$ = 21.99 |

It can be well seen that the characteristic radiation of 50Sn is lying between the absorption and emission energy levels of 47Ag. 48Cd and 49In and their compounds are suitable pre-exciting elements to 47Ag. Characteristic radiation emitted by 37Rb performs pre-exciting of 35Br.

In the embodiment according to FIG. 3 before the first layer group 61 layers 18 with 82Pb material are arranged for absorbing the scattered radiation coming from the object examined and the environment, as well as for the simultaneous emission of secondary radiation. Behind the target 7 layers 19 with 82Pb material are arranged for absorbing the re-scattered radiation. Immediately before the target 7 one or more layers 20 containing 82Pb are arranged for absorbing the scattered radiation arising in the layer groups 61, . . . 64.

The embodiment according to FIG. 3 can be well used for radiographs serving for industrial purposes. In this case total thickness of the layers 18 amounts to 100 to 500 $\mu$m, while this layer group is composed of 82Pb layers of the thickness of 1 $\mu$m or even less. Layers 19 can be similarly formed. The single layer 20 may be a 82Pb layer of the thickness of 10 to 30 $\mu$m. Layer groups 61, . . . 64 are of the thickness of 25 to 125 $\mu$m each, being formed of layers of 51Sb, 50Sn, 38Sr and 37Rb, respectively, in a thickness of 1 $\mu$m or even less. Between adjacent layers e.g. Al$_2$O$_3$ separating layers of 0.1 $\mu$m are to be found. Any element of the series can form a separating layer, so e.g. in the layer group 61 separating layers of 50Sn of the thickness 0.1 $\mu$m can be used between the layers of 51Sb. For the sake of order it should be mentioned that the thickness of the layer groups 61, . . . 64 need not be necessarily identical, within one layer group layers may have different thicknesses.

The modifying body according to the invention can be realized differently from the embodiments shown in the drawings. So e.g. it can be prepared as a flexible sheet, which is well matching to targets having not a plain surface.

I claim:

1. A method for influencing the effect of X-ray or gamma radiation on a target sensitive to the radiation, the method comprising the steps of: irradiating the target with an X-ray or gamma radiation beam and disposing a modifying body in front of and adjacent to the target in the path of the radiation beam, wherein a transmission direction is defined along the path from the modifying body to the target, and wherein said modifying body comprises at least two contiguously disposed layer groups, each of said layer groups (e.g., 32) comprising a plurality of superposed metallic layers and separating layers therebetween, said metallic layers being provided for emitting a secondary radiation under the influence of the X-ray or gamma radiation, or the secondary radiation of the metallic layers in a previous layer group (e.g., 31) with respect to the transmission direction, respectively, the energy of the secondary radiation emitted by said metallic layers being above the absorption energy level defined by the electron shell K of an element being present in the subsequent layer group (e.g., 33) with respect to the transmission direction, or in the target, respectively.

2. The method as claimed in claim 1, wherein said modifying body further comprises at least one further layer group (62, 64) emitting a secondary radiation, the energy of which is lying between the absorption energy level and the emission energy level defined by the electron shell K of an element being present in the metallic layers of the subsequent layer group with respect to the transmission direction, or in the target, respectively.

3. The method as claimed in claim 1 or 2, wherein said superposed metallic layers in each layer group contain a metal element with a lower atomic number than that of a metal element being present in the superposed metallic layers in the previous layer group with respect to the transmission direction.

4. The method as claimed in claim 1 or 2, characterized by further disposing said modifying body between two conductive layers and generating an electric field between said two conductive layers, the direction of the field being substantially parallel to the transmission direction.

5. The method as claimed in claim 1, wherein said modifying body comprises at least three of said layer groups.

6. A modifying body for influencing the effect of X-ray or gamma radiation on a target sensitive to the radiation, wherein a transmission direction is defined in a direction corresponding to that of the X-ray or gamma radiation travelling through said modifying body, said modifying body comprising at least two layer groups disposed contiguously, each of said layer groups comprising a plurality of superposed metallic layers and separating layers disposed therebetween, said metallic layers being provided for emitting a secondary radiation under the influence of the X-ray or gamma radiation, or the secondary radiation of the metallic layers in a previous layer group with respect to the transmission direction, respectively, the energy of the secondary radiation being above the absorption energy level defined by the electron shell K of an element being present in the metallic layers of the subsequent layer group with respect to the transmission direction, or in the target, respectively.

7. The modifying body as claimed in claim 6, further comprising at least one further layer group comprising a plurality of superposed metallic layers and separating layers therebetween, said metallic layers emitting a secondary radiation, the energy of which is lying between the absorption energy level and the emission energy level defined by the electron shell K of an element being present in the metallic layers of the subsequent layer group with respect to the transmission direction, or in the target, respectively.

8. The modifying body as claimed in claim 6 or 7, wherein the thickness of each of said metallic layers in said layer groups is less than 30 $\mu$m.

9. The modifying body as claimed in claim 6 or 7, wherein the thickness of each of said metallic layers in said layer groups lies in the range between 0.1 and 10 $\mu$m and the thickness of each of said layer groups lies in the range between 25 and 125 $\mu$m.

10. The modifying body as claimed in claim 6 or 5, further comprising one or more layers or coatings consisting of graphite or carbon or carbon compound, producing Compton-electrons.

11. The modifying body as claimed in claim 6 or 7, wherein a surface of at least one of said metallic layers in at least one of said layer groups is provided with a substantially monoatomic coating consisting of an alkali metal or alkali-earth metal or the oxides thereof or any other compound thereof, facilitating electron departure.

12. The modifying body as claimed in claim 6 or 7, further comprising two electrically conductive layers, and means for electrically insulating said two layers from the other layers in said layer groups, wherein two conductive layers are disposed so as to border said layer groups, each of said conductive layers being provided with an electric contact and a terminal connected thereto.

13. The modifying body as claimed in claim 6 or 7, wherein each of said layer groups is applied onto a carrier sheet which is substantially transparent to X-ray or gamma radiation.

14. The modifying body as claimed in claim 6 or 7, wherein all of said layer groups are applied onto one single carrier sheet which is transparent to X-ray or gamma radiation.

15. The modifying body as claimed in claim 13, wherein said carrier sheet is made of paper or plastic or aluminum foil.

16. The modifying body as claimed in claim 13, wherein said metallic layers and said separating layers in each of said layer groups are applied onto said carrier sheet by vacuum deposition.

17. The modifying body as claimed in claim 6, wherein said target includes an AgBr film, and the energy of the secondary radiation emitted by the metal element of the layer group which is last in the transmission direction is higher by a maximum of 100% than the absorption energy level of the element of the target.

18. The modifying body as claimed in claim 6 or 7, wherein said target includes an AgBr film, a first one of said layer groups comprises metallic layers containing antimony or its compound, a second one of said layer groups comprises metallic layers containing strontium or its compound and said second one of said layer groups is disposed after said first one with respect to the transmission direction.

19. The modifying body as claimed in claim 18, including a third one of said layer groups which third one comprises metallic layers containing at least one of the elements selected from a group of cadmium, indium and tin or at least one of their compounds, wherein said third one of said layer groups is disposed between said first and second layer groups.

20. The modifying body as claimed in claim 19, including a fourth one of said layer groups which fourth one comprises metallic layers containing rubidium or its compound, wherein said fourth layer group is disposed after said second layer group with respect to the transmission direction.

21. The modifying body as claimed in claim 6, wherein said modifying body comprises at least three of said layer groups.

22. The modifying body as claimed in claim 6, wherein said energy of the secondary radiation is higher by a maximum of 50% than said absorption energy level.

23. A method for recording an image of an object formed on a target by X-ray or gamma radiation, said method comprising the steps of: irradiating the target by directing an X-ray or gamma radiation beam through the object and disposing a modifying body between the object and the target, adjacent to the target, in the path of the radiation beam, wherein a transmission direction is defined along the path from the object to the target, and wherein said modifying body comprises at least two contiguously disposed layer groups, each of said layer groups comprising a plurality of superposed metallic layers with separating layers therebetween, said metallic layers being provided for emitting a secondary radiation under the influence of the X-ray or gamma radiation, or the secondary radiation of the metallic layers in a previous layer group with respect to the transmission direction, respectively, the energy of the secondary radiation being above the absorption energy level defined by the electron shell K of an element being present in the metallic layers of the subsequent layer group with respect to the transmission direction, or in the target, respectively.

24. The method as claimed in claim 23, wherein said modifying body further comprises at least one further layer group comprising a plurality of superposed metallic layers and separating layers therebetween, said metallic layers being provided for emitting a secondary radiation, the energy of which is lying between the absorption energy level and the emission energy level defined by the electron shell K of an element being present in the metallic layers of the subsequent layer group with respect to the transmission direction, or in the target, respectively.

25. The method as claimed in claim 23 or 24, wherein said superposed metallic layers in each layer group contain a metal element with a lower atomic number than that of a metal element being present in the superposed metallic layers in the previous layer group with respect to the transmission direction.

26. The method as claimed in claim 23 or 24, characterized by further disposing said modifying body between two conductive layers and generating an electric field between said two conductive layers, the direction of the field being substantially parallel to the transmission direction.

27. The method as claimed in claim 23, wherein said modifying body comprises at least three of said layer groups.

* * * * *